(12) United States Patent
Terranova et al.

(10) Patent No.: US 7,638,657 B2
(45) Date of Patent: Dec. 29, 2009

(54) PREPARATION OF 3-[5'-(3,4-BIS(HYDROXYMETHYL)BENZYLOXY)-2'-ETHYL-2-PROPYLBIPHENYL-4-YL]PENTAN-3-OL

(75) Inventors: Eric Terranova, Magagnosc (FR); Sebastien Daver, Antibes (FR); Christine Marty, Biot (FR); Jean-Claude Pascal, Nice (FR)

(73) Assignee: Galderma Research & Development, Biot (FR)

( * ) Notice: Subject to any disclaimer, the term of this patent is extended or adjusted under 35 U.S.C. 154(b) by 190 days.

(21) Appl. No.: 11/802,029

(22) Filed: May 18, 2007

(65) Prior Publication Data

US 2007/0282136 A1 Dec. 6, 2007

Related U.S. Application Data

(63) Continuation of application No. PCT/FR2005/002856, filed on Nov. 17, 2005.

(30) Foreign Application Priority Data

Nov. 19, 2004 (FR) .................................. 04 12325

(51) Int. Cl.
*C07C 43/20* (2006.01)
*C07C 41/01* (2006.01)
*C07C 37/00* (2006.01)

(52) U.S. Cl. ........................ 568/643; 568/662; 568/747

(58) Field of Classification Search ....................... None
See application file for complete search history.

(56) References Cited

U.S. PATENT DOCUMENTS 6,924,400 B2   8/2005   Bernardon et al.
2007/0015931 A1   1/2007   Terranova et al.

FOREIGN PATENT DOCUMENTS

WO   WO 03/050067 A2   6/2003
WO   WO 2005/058918 A1   6/2005
WO   WO 2005/061520 A1   7/2005

*Primary Examiner*—Rosalynd Keys
(74) *Attorney, Agent, or Firm*—Buchanan, Ingersoll & Rooney P.C.

(57) ABSTRACT

3-[5'-(3,4-bis(hydroxymethyl)benzyloxy)-2'-ethyl-2-propyl-biphenyl-4-yl]pentan-3-ol is prepared from the novel intermediate, 6-ethyl-4'-(1-ethyl-1-hydroxypropyl)-2'-propylbiphenyl-3-ol.

16 Claims, 1 Drawing Sheet

Figure 1:
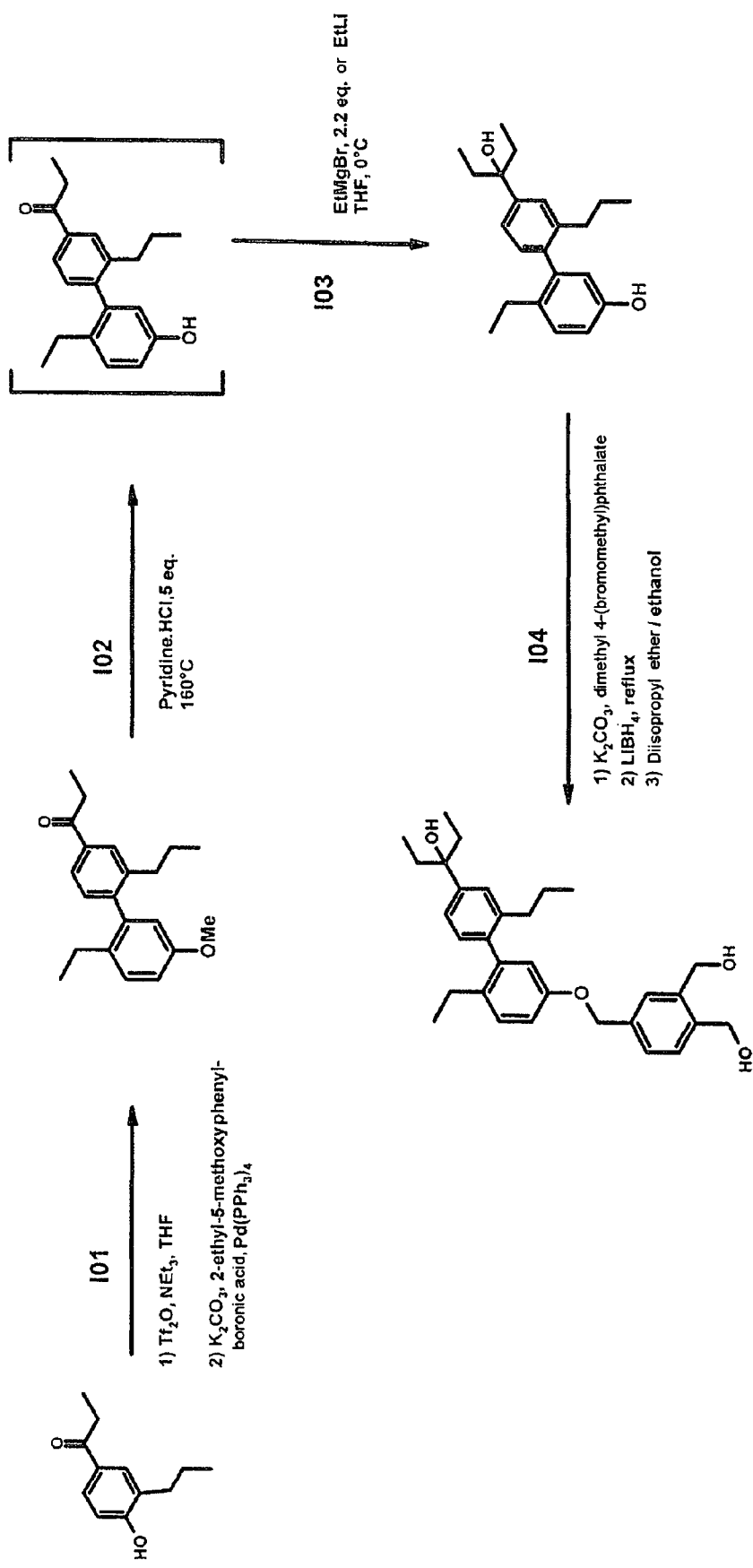

PREPARATION OF 3-[5'-(3,4-BIS(HYDROXYMETHYL)BENZYLOXY)-2'-ETHYL-2-PROPYLBIPHENYL-4-YL]PENTAN-3-OL

CROSS-REFERENCE TO PRIORITY/PCT APPLICATIONS

This application claims priority under 35 U.S.C. § 119 of FR 04/12325, filed Nov. 19, 2004, and is a continuation of PCT/FR 2005/002856, filed Nov. 17, 2005, and designating the United States (published in the French language on May 26, 2006 as WO 2006/053985 A1; the title and abstract were also published in English), each hereby expressly incorporated by reference in its entirety and each assigned to the assignee hereof.

BACKGROUND OF THE INVENTION

1. Technical Field of the Invention

The present invention relates to a process for the preparation of 3-[5'-(3,4-bis(hydroxymethyl)benzyloxy)-2'-ethyl-2-propylbiphenyl-4-yl]pentan-3-ol of formula:

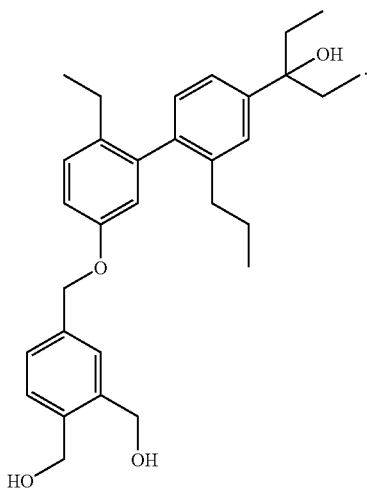

2. Description of Background and/or Related and/or Prior Art

The compounds of the family of the above 3-[5'-(3,4-bis(hydroxymethyl)benzyloxy)-2'-ethyl-2-propylbiphenyl-4-yl]pentan-3-ol and their applications in human medicine have been described by the assignee hereof in WO 03/050067.

In this patent application, the synthesis of 3-[5'-(3,4-bis(hydroxymethyl)benzyloxy)-2'-ethyl-2-propylbiphenyl-4-yl]pentan-3-ol is carried out in 17 stages. The majority of the intermediates generated in this synthesis are purified by chromatography on a silica column, making it difficult to manufacture this product on a large scale.

In addition, due to this large number of stages, the overall yield of this synthesis is very low, less than 0.5%, and the manufacturing times are very long.

SUMMARY OF THE INVENTION

A novel process for the preparation of 3-[5'-(3,4-bis(hydroxymethyl)benzyloxy)-2'-ethyl-2-propylbiphenyl-4-yl]pentan-3-ol in four stages has now been developed, making it possible to overcome or ameliorate the difficulties and drawbacks indicated above.

The present invention thus features a process for the preparation of 3-[5'-(3,4-bis(hydroxymethyl)benzyloxy)-2'-ethyl-2-propylbiphenyl-4-yl]pentan-3-ol, which comprises the following stages:

a) conversion of 1-(4-hydroxy-3-propylphenyl)propan-1-one to give trifluoromethanesulfonic acid 4-propionyl-2-(n-propyl)phenyl ester, followed in situ by a reaction of Suzuki type with 2-ethyl-5-methoxyphenylboronic acid;

b) demethylation of 1-(2'-ethyl-5'-methoxy-2-propylbiphenyl-4-yl)propan-1-one by heating with an excess of pyridine salts;

c) conversion of 1-(2'-ethyl-5'-hydroxy-2-propylbiphenyl-4-yl)propan-1-one to give 6-ethyl-4'-(1-ethyl-1-hydroxypropyl)-2'-propylbiphenyl-3-ol by reaction with ethylmagnesium bromide or ethyllithium; and d) condensation of 6-ethyl-4'-(1-ethyl-1-hydroxypropyl)-2'-propylbiphenyl-3-ol with dimethyl 4-(bromomethyl)phthalate, followed in situ by a reduction reaction with lithium borohydride.

BRIEF DESCRIPTION OF THE FIGURE OF DRAWING

The FIGURE of Drawing illustrates a variety of reaction schemes for the ultimate preparation of the subject 3-[5'-(3,4-bis(hydroxymethyl)benzyloxy)-2'-ethyl-2-propylbiphenyl-4-yl]pentan-3-ol.

DETAILED DESCRIPTION OF BEST MODE AND SPECIFIC/PREFERRED EMBODIMENTS OF THE INVENTION

More specifically, the process according to the invention comprises the following detailed stages:

The first stage of this process (stage a) above or 101 in the FIGURE of Drawing is a one pot reaction for the conversion of 1-(4-hydroxy-3-propylphenyl)propan-1-one (prepared according to Demerseman et al., *Bull. Soc. Chim. Fr.*, 1963, 2559-2562, or Stoughton, Baltzly and Bass, *J. Am. Chem. Soc.*, 56, 1934, 2007) by reaction with trifluoromethanesulfonic anhydride ($Tf_2O$) in the presence of triethylamine ($NEt_3$) to provide its derivative trifluoromethanesulfonic acid 4-propionyl-2-(n-propyl)phenyl ester, followed by an in situ condensation of Suzuki type with 2-ethyl-5-methoxyphenylboronic acid (prepared according to a process described in FR-2,863,613) in the presence of $K_2CO_3$ and of a catalytic amount of $PdCl_2(PPh_3)_2$ or $Pd(PPh_3)_4$.

This one pot reaction is carried out in solvents such as tetrahydrofuran (THF), dimethylformamide (DMF), aromatic solvents, such as toluene, ethereal solvents, such as diisopropyl ether, halogenated solvents, such as chloroform, or alkanes, such as pentane, hexane or heptane. The solvents preferably used in this reaction are DMF and/or toluene.

The reaction is carried out at temperatures of from 5° to 140° C., preferably at about 120° C.

The amounts of catalyst $PdCl_2(PPh_3)_2$ or $Pd(PPh_3)_4$ employed in this reaction can vary from 0.001 to 0.05 molar equivalent with respect to the amount of 1-(4-hydroxy-3-propylphenyl)propan-1-one. Preferably, from 0.01 to 0.05 molar equivalent of $PdCl_2(PPh_3)_2$ or $Pd(PPh_3)_4$ is employed.

In the second stage (stage b) above or 102 in the FIGURE of Drawing), 1-(2'-ethyl-5'-methoxy-2-propylbiphenyl-4-yl)propan-1-one is subjected to a demethylation reaction with a pyridine salt. The reaction is carried out without solvent at temperatures of from 80° to 200° C., preferably at about 170° C.

The pyridine salts used in this reaction can be the hydrochloride, the hydrobromide or the hydriodide and can vary from 1 to 10 molar equivalents. Preferably, about 5 molar equivalents will be used.

The third stage (stage c) above or 103 in the FIGURE of Drawing) is the conversion of 1-(2'-ethyl-5'-hydroxy-2-propylbiphenyl-4-yl)propan-1-one to give a novel compound, 6-ethyl-4'-(1-ethyl-1-hydroxypropyl)-2'-propylbiphenyl-3-ol, by reaction with ethylmagnesium bromide or with ethyllithium.

The solvents preferably used in this reaction are ethers, such as ethyl ether, tert-butyl dimethyl ether or tetrahydrofuran.

The reaction is carried out at temperatures of from −20° C. to 20° C., preferably at about 0° C.

The amounts of ethylmagnesium bromide or of ethyllithium used in this reaction can vary from 2 to 5 molar equivalents. Preferably, 2.2 molar equivalents will be used.

In the following stage (stage d) above or 104 in the FIGURE of Drawing, 6-ethyl-4'-(1-ethyl-1-hydroxypropyl)-2'-propylbiphenyl-3-ol is condensed with dimethyl 4-(bromomethyl)phthalate (prepared according to a method analogous to that described by E. H. White, D. F. Roswell and O. C. Zafiriou in *J. Org. Chem.*, 34 (8), 2462-2468, 1969, and J. W. Leon, M. Kawa and J. M. J. Frechet in *J. Amer. Chem. Soc.*, 118, 8847-8859, 1996) in the presence of potassium carbonate (K$_2$CO$_3$) in tetrahydrofuran at reflux. The two carboxyl functional groups are subsequently reduced in situ by the addition of lithium borohydride (LiBH$_4$) and then heating at reflux of the tetrahydrofuran.

The first reaction can be catalyzed by phase transfer agents, such as Aliquat 336 or tetrabutylammonium bromide, in the presence of potassium iodide.

The present invention also features the novel compound 6-ethyl-4'-(1-ethyl-1-hydroxypropyl)-2'-propylbiphenyl-3-ol having the structure:

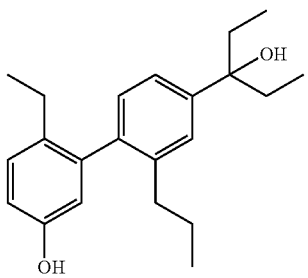

and to its process for the preparation hereof.

This invention thus also features the process for the conversion of 1-(2'-ethyl-5'-hydroxy-2-propylbiphenyl-4-yl)propan-1-one to give 6-ethyl-4'-(1-ethyl-1-hydroxypropyl)-2'-propylbiphenyl-3-ol by reaction with ethylmagnesium bromide or with ethyllithium.

The solvents preferably used in this reaction are ethers, such as ethyl ether, tert-butyl dimethyl ether or tetrahydrofuran.

The reaction is carried out at temperatures of from −20° C. to 20° C., preferably at about 0° C. The amounts of ethylmagnesium bromide or of ethyllithium used in this reaction can vary from 2 to 5 molar equivalents. Preferably, 2.2 molar equivalents will be used.

After treatment, 6-ethyl-4'-(1-ethyl-1-hydroxypropyl)-2'-propylbiphenyl-3-ol is crystallized from diisopropyl ether or dichloromethane, making it possible to obtain this product with a purity of greater than 99%.

The present invention also features the use of 6-ethyl-4'-(1-ethyl-1-hydroxypropyl)-2'-propylbiphenyl-3-ol in the preparation of 3-[5'-(3,4-bis(hydroxymethyl)benzyloxy)-2'-ethyl-2-propylbiphenyl-4-yl]pentan-3-ol.

In order to further illustrate the present invention and the advantages thereof, the following specific example is given, it being understood that same is intended only as illustrative and in nowise limitative. In said examples to follow, all parts and percentages are given by weight, unless otherwise indicated.

EXAMPLE

Synthesis of 3-[5'-(3,4-bis(hydroxymethyl)benzyloxy)-2'-ethyl-2-propylbiphenyl-4-yl]pentan-3-ol Preparation of 1-(2'-ethyl-5'-methoxy-2-propylbiphenyl-4-yl)-propan-1-one 203 g of 1-(4-hydroxy-3-propylphenyl)propan-1-one and 1 liter of toluene are charged into a 4 liter reactor under nitrogen. The medium is cooled to approximately −5° C. and then the rapid addition is carried out of 176 ml of triethylamine and then of 196 ml of trifluoromethanesulfonic anhydride over 1 hour at from −5° C. to +1° C. After stirring for 30 min, 1 liter of a 2M K$_2$CO$_3$ solution is introduced, followed by 190 g of 2-ethyl-5-methoxyphenylboronic acid in solution in 610 ml of dimethylformamide. 12 g of tetrakis(triphenylphosphine)palladium(0) are added and the reaction medium is heated at reflux for 2 h. After being brought back to ambient temperature, the reaction medium is washed 3 times with 610 ml of a saturated NH$_4$Cl solution and then with 610 ml of water. The solvents are evaporated from the organic phase under vacuum. The crude product obtained is taken up in 1 volume of dichloromethane, which is deposited on 3 times its weight of silica. Elution is carried out with 16 volumes of methylene chloride. After evaporating the solvent, 335 g of 1-(2'-ethyl-5'-hydroxy-2-propylbiphenyl-4-yl)propan-1-one are obtained (beige oil; 100% yield).

Preparation of 1-(2'-ethyl-5'-hydroxy-2-propylbiphenyl-4-yl)propan-1-one 413 g (1.33 mol) of 1-(2'-ethyl-5'-methoxy-2-propylbiphenyl-4-yl)propan-1-one and 768 g (6.64 mol) of pyridine hydrochloride are placed in a round-bottomed flask. The mixture is heated at 160°-170° C. for 4 hours with stirring. The reaction medium is allowed to return to 100°-110° C. and 800 ml of water are added. The mixture is cooled to 30° C. and extracted with 1.6 liters of ethyl acetate. After separating by settling, the aqueous phase is extracted with 600 ml of ethyl acetate. The organic phases are combined and washed twice with 800 ml of water. After evaporating under reduced vacuum, 410 g of 1-(2'-ethyl-5'-hydroxy-2-propylbiphenyl-4-yl)propan-1-one are obtained in the form of an oil.

Preparation of 6-ethyl-4'-(1-ethyl-1-hydroxypropyl)-2'-propylbiphenyl-3-ol 370 g (1.248 mol) of 1-(2'-ethyl-5'-hydroxy-2-propylbiphenyl-4-yl)propan-1-one in solution in 3.7 liters of tetrahydrofuran are placed in a reactor. 915 ml of a 3M solution of ethylmagnesium bromide in ethyl ether are slowly run into this solution cooled to −10° C. At the end of the addition, the reaction mixture is kept stirred for 1 hour and then transferred onto 5 liters of a 2.5 molar solution of ammonium chloride in water. The organic phase is separated by settling and washed twice with 800 ml of water. After evaporating under reduced vacuum, the residue is dissolved with 2.75 liters of methylene chloride at reflux. The medium is allowed to return to ambient temperature with stirring and is then cooled to 5° C. The crystals are filtered off and then dried under vacuum. 260 g (64%) of 6-ethyl-4'-(1-ethyl-1-hydroxypropyl)-2'-propylbiphenyl-3-ol are obtained. Melting point: 130° C. $^1$H NMR (d$_6$-DMSO) (ppm): 0.67-0.74, m, 9H; 0.9, t, 3H; 1.38, m, 2H; 1.71-1.77, m, 4H; 2.13-2.35, m, 4H; 4.48, s, 1H; 6.45, d, 1H; 6.70, dd, 1H; 6.94, d, 1H; 7.07, d, 1H; 7.18, dd, 1H; 7.26, s, 1H; 9.16, s, 1H Synthesis of 3-[5'-(3,4-bis(hydroxymethyl)benzyloxy)-2'-ethyl-2-propylbiphenyl-4-yl]pentan-3-ol 40 g (0.123 mol) of 6-ethyl-4'-(1-ethyl-1-hydroxypropyl)-2'-propylbiphenyl-3-ol, 37 g (0.129 mol) of dimethyl 4-(bromomethyl)phthalate, 17.8 g (0.129 mol) of potassium carbonate, 500 mg of Aliquat 336 and 100 mg of potassium iodide are introduced into 400 ml of tetrahydrofuran in a round-bottomed flask equipped with a mechanical stirrer. The reaction mixture is heated at reflux for 6 hours. After returning to ambient temperature, 4 g (0.184 mol) of lithium borohydride are added portionwise. Heating is again carried out for 4 hours. The medium is allowed to return to ambient temperature and is then slowly transferred onto 600 ml of ice-cold water. After stirring for two hours, the organic phase is extracted with 100 ml of ethyl acetate and washed twice with 200 ml of water. The organic phase is evaporated under reduced vacuum and the residue is dissolved in a diisopropyl ether/ethanol mixture at 50° C.

After stirring overnight, the crystals are filtered off and dried under vacuum. 41.6 g (71%) of 3-[5'-(3,4-bis(hydroxymethyl)benzyloxy)-2'-ethyl-2-propylbiphenyl-4-yl]pentan-3-ol are obtained.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of 3-[5'-(3,4-bis(hydroxymethyl)benzyloxy)-2'-ethyl-2-propylbiphenyl-4-yl]pentan-3-ol having the structure:

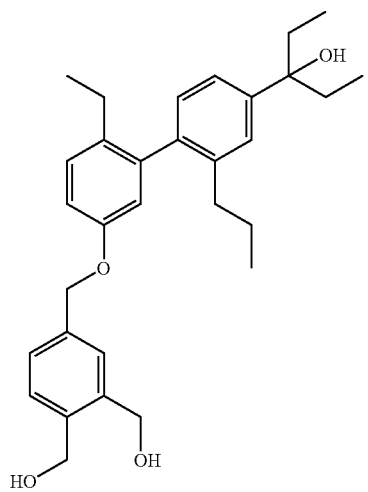

which comprises the following 4 stages:
 a) converting 1-(4-hydroxy-3-propylphenyl)propan-1-one into trifluoromethanesulfonic acid 4-propionyl-2-(n-propyl)phenyl ester, followed by reacting same with 2-ethyl-5-methoxyphenylboronic acid;
 b) demethylation of 1-(2'-ethyl-5'-methoxy-2-propylbiphenyl-4-yl)propan-1-one by heating with an excess of pyridine salts;
 c) converting 1-(2'-ethyl-5'-hydroxy-2-propylbiphenyl-4-yl)propan-1-one into 6-ethyl-4'-(1-ethyl-1-hydroxypropyl)-2'-propylbiphenyl-3-ol by reaction with ethylmagnesium bromide or with ethyllithium; and
 d) condensation of 6-ethyl-4'-(1-ethyl-1-hydroxypropyl)-2'-propylbiphenyl-3-ol with dimethyl 4-(bromomethyl)phthalate, followed in situ by a reduction reaction with lithium borohydride.

2. The process as defined by claim 1, wherein the reaction of stage a) comprises a reaction for the conversion of 1-(4-hydroxy-3-propylphenyl)propan-1-one by reaction with trifluoromethanesulfonic anhydride (Tf$_2$O) in the presence of triethylamine (NEt$_3$) to give its derivative trifluoromethanesulfonic acid 4-propionyl-2-(n-propyl)phenyl ester, followed by a condensation of Suzuki type with 2-ethyl-5-methoxyphenylboronic acid, and in that the said reactions of stage a) are carried out in situ in the presence of K$_2$CO$_3$ and of a catalytic amount of PdCl$_2$(PPh$_3$)$_2$ or Pd(PPh$_3$)$_4$, in a tetrahydrofuran (THF) or dimethylformamide (DMF) solvent, or an aromatic solvent, or an ethereal solvent, or a halogenated solvent, or an alkane solvent.

3. The process as defined by claim 2, wherein the reaction of stage a) is carried out at temperatures ranging from 5° to 140° C. and that the catalytic amounts of PdCl$_2$(PPh$_3$)$_2$ or Pd(PPh$_3$)$_4$ range from 0.01 to 0.05 molar equivalent.

4. The process as defined by claim 1, wherein the pyridine salt of stage b) comprises a pyridine hydrochloride, hydrobromide or hydriodide at a concentration ranging from 1 to 10 molar equivalents.

5. The process as defined by claim 1, wherein the pyridine salt of stage b) is employed at a concentration of about 5 molar equivalents.

6. The process as defined by claim 1, wherein stage b) is carried out in the absence of solvent.

7. The process as defined by claim 1, wherein stage b) is carried out at temperatures ranging from 80° to 200° C.

8. The process as defined by claim 7, wherein stage b) is carried out at a temperature of about 170° C.

9. The process as defined by claim 1, wherein stage c) comprises the conversion of 1-(2'-ethyl-5'-hydroxy-2-propylbiphenyl-4-yl)propan-1-one to give 6-ethyl-4'-(1-ethyl-1-hydroxypropyl)-2'-propylbiphenyl-3-ol by reaction with ethylmagnesium bromide or with ethyllithium in the presence of a solvent.

10. The process as defined by claim 1, wherein stage d) comprises the condensation of 6-ethyl-4'-(1-ethyl-1-hydroxypropyl)-2'-propylbiphenyl-3-ol with dimethyl 4-(bromomethyl)phthalate in the presence of potassium carbonate (K$_2$CO$_3$) in tetrahydrofuran at reflux, with the two carboxyl functional groups subsequently being reduced in situ by the addition of lithium borohydride (LiBH$_4$) and then heating at reflux of the tetrahydrofuran.

11. A process for the preparation of 6-ethyl-4'-(1-ethyl-1-hydroxypropyl)-2'-propylbiphenyl-3-ol having the structure:

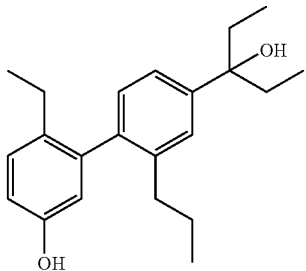

from 1-(2'-ethyl-5'-hydroxy-2-propylbiphenyl-4-yl)propan-1-one by addition thereto of ethylmagnesium bromide or of ethyllithium in the presence of a solvent.

12. The process as defined by claim 11, wherein the solvent comprises an ether.

13. The process as defined by claim 11, wherein the reaction is carried out at a temperature ranging from −20° C. to 20° C.

14. The process as defined by claim 11, wherein the reaction is carried out at a temperature of about 0° C.

15. The process as defined by claim 11, wherein the amounts of ethylmagnesium bromide or of ethyllithium range from 2 to 5 molar equivalents.

16. The process as defined by claim 11, wherein the amount of ethylmagnesium bromide is about 2.2 molar equivalents.

* * * * *